(12) United States Patent
Petersen et al.

(10) Patent No.: US 6,525,095 B1
(45) Date of Patent: Feb. 25, 2003

(54) PROPIONATE FEED SUPPLEMENT

(75) Inventors: Mark K. Petersen, Las Cruces, NM (US); Jason E. Sawyer, Clayton, NM (US); Richard C. Waterman, Las Cruces, NM (US); Dean E. Hawkins, Las Cruces, NM (US)

(73) Assignee: New Mexico State University Technology Transfer Corporation, Las Cruces, NM (US)

( * ) Notice: Subject to any disclaimer, the term of this patent is extended or adjusted under 35 U.S.C. 154(b) by 0 days.

(21) Appl. No.: 09/903,088

(22) Filed: Jul. 10, 2001

Related U.S. Application Data

(60) Provisional application No. 60/217,212, filed on Jul. 10, 2000, and provisional application No. 60/236,431, filed on Sep. 28, 2000.

(51) Int. Cl.[7] ................................................ A61K 31/19
(52) U.S. Cl. ...................................................... 514/557
(58) Field of Search .......................................... 514/557

(56) References Cited

U.S. PATENT DOCUMENTS

| | | | |
|---|---|---|---|
| 4,981,105 A | * | 1/1991 | Petersen ...................... 119/74 |
| 5,635,535 A | | 6/1997 | Wagstaff |
| 5,672,366 A | | 9/1997 | Petersen |
| 5,846,581 A | | 12/1998 | Catron |
| 5,955,122 A | | 9/1999 | Petersen |
| 6,204,277 B1 | * | 3/2001 | Shikai et al. ................ 514/374 |

OTHER PUBLICATIONS

Goff, J.P., et al., "Field Trials of an Oral Calcium Propionate Paste as an Aid to Prevent Milk Fever in Periparturient Dairy Cows," *J. Dairy Sci,* vol. 79, pp 378–383.

KEMIN Product Profile for NutroCAL™ Dry Gluconeogenic Supplement.

* cited by examiner

*Primary Examiner*—Kevin E. Weddington
(74) *Attorney, Agent, or Firm*—Deborah A. Peacock

(57) ABSTRACT

A supplement for ruminants comprising propionate. The propionate supplement is preferably combined with a protein feed supplement to reduce insulin insensitivity and increase body weight in ruminants.

19 Claims, No Drawings

PROPIONATE FEED SUPPLEMENT

CROSS-REFERENCE TO RELATED APPLICATIONS

This application is related to U.S. Pat. No. 5,672,366, entitled "Method of Improving Efficiency in Ruminants" issued on Sep. 30, 1997, and U.S. Pat. No. 5,955,122, entitled "Method of Improving Efficiency in Ruminants," issued on Sep. 21, 1999, the specifications and teachings of which are incorporated herein by reference.

This application claims priority both to U.S. Provisional Patent Application Ser. No. 60/217,212, entitled "Method to Reduce Insulin Sensitivity in Ruminants," filed on Jul. 10, 2000, and U.S. Provisional Patent Application Ser. No. 60/236,431, entitled "Method to Reduce Insulin Insensitivity in Ruminants," filed Sep. 28, 2000, and the specifications and teachings thereof are incorporated herein by reference.

BACKGROUND OF THE INVENTION

1. Field of the Invention (Technical Field)

The present invention relates to a propionate feed for ruminants.

2. Background Art

The following described patent is directed to the use of calcium propionate in humans for exercise and dieting. U.S. Pat. No. 5,635,535, entitled "Method for Increasing Blood Glucose Levels," to Wagstaff, issued Jun. 3, 1997 ('535 Patent), discloses a method of using calcium propionate as a gluconeogenic compound to increase blood glucose levels while metabolizing body fat. The method includes the step of subjecting a human to conditions where the body starts to use stored fat as an energy source. According to the disclosure, propionic acid is the active ingredient that is converted to glucose. It is also a co-factor that assists with the conversion of stored body fats to glucose rather than ketones. Its gluconeogenic action is eliminated when sufficient food is consumed. The calcium propionate is administered on the order of 100 to 1000 mg per day. The '535 Patent does not disclose glucose uptake by the human body, insulin, or diabetic conditions. Rather, the '535 Patent is directed to maintaining blood glucose levels during exercise and dieting. Body physiology during exercise and dieting, which are short term conditions, differs considerably from the physiological state produced by undernutrition, especially chronic undernutrition. Undernutrition can greatly effect the physiological response to insulin, whereas, strenuous exercise and reasonable dieting do not. The '535 Patent does not teach or suggest a method to treat undernutrition in ruminants wherein insulin response is impaired.

U.S. Pat. No. 5,846,581, entitled "Chromium (III) Salts of Short Chain Fatty Acids Composition For Use in Animal Feeds," to Catron, issued Dec. 8, 1998 ('581 Patent), discloses the use of trace metal salts (e.g., chromium (III) and manganese (II)), of short chain fatty acids as nutritional supplements. The disclosure focuses on eliminating and/or greatly reducing the presence of chromium (VI). The '581 Patent discloses the use of propionate as a carrier or chelant, because of fewer undesirable traits for the consummation of the final product. In Example 7, the '585 Patent discloses experiments wherein Test 1 added chromium (III) propionate at a level of 200 parts per billion (ppb) chromium to a corn-soybean swine feed and Test 2 added chromium (III) tripicolinate at a level of 200 ppb chromium to a corn-soybean swine feed. When fed to swine, the feeds resulted in a decrease in average daily gain and average feed intake per day, but not feed efficiency. Total insulin remained unaffected. During the insulin challenge, glucose clearance was increased slightly more in the propionate test and glucose half-life was decreased regardless of whether propionate or tripicolinate was used as a chelant. Overall, the results indicate that use of a propionate chelant enhances chromium bioavailability. At such low levels (200 ppb Cr as chromium propionate), the results do not support any conclusion as to the effect of propionate absent chromium. Again, according to Example 7, the mole ratio of propionate to chromium is approximately 5.7 to 1, thus, approximately 1 ppm of propionate was added to the feed (1 mg propionate per kilogram feed).

Kemin Industries, Inc. manufactures a calcium propionate product called NutroCAL that is used to prevent ketosis in dairy cows. The suggested dosage is 125 grams (¼ lb.) per head per day. This supplement is not used for cows that are already insulin insensitive (e.g. range beef cows).

A calcium propionate paste has been reported as a useful aid to prevent milk fever and hypocalcemia in periparturient dairy cows. See Goff et al., "Field Trials of an Oral Calcium Propionate Paste as an Aid to Prevent Milk Fever in Periparturient Dairy Cows, *Journal of Dairy Science*, 79:378–383 (1996). The dosage was two tubes of calcium propionate (each tube containing 3 grams of calcium and 134 grams of propionate) at calving and again 12 hours after calving.

None of these references disclose the use of propionate for ruminants who are insulin insensitive (e.g. range sheep and cattle) in order to reduce the insulin insensitivity and increase body weight.

SUMMARY OF THE INVENTION
(DISCLOSURE OF THE INVENTION)

The present invention is directed to a supplement for ruminants who are already insulin insensitive, that reduces insulin insensitivity and increases body weight. This supplement is a large dose of propionate, e.g. calcium propionate, sodium propionate, propionic acid, and the like. The preferred dosing or percentages are as follows: 25–200 grams, preferably 50–150 grams, and most preferably 80–120 grams of calcium propionate per day for a typical cow weighing approximately 550 kilograms. Since there is approximately 80 percent propionate in calcium propionate, the preferred ranges are 20–160 grams of propionate, preferably 40–120 grams of propionate, and most preferably 64–96 grams of propionate per day for a typical cow weighing approximately 550 kilograms. This works out to preferred ranges of 0.04–0.29 grams of propionate per kilogram of animal body weight, preferably 0.07–0.22 grams of propionate per kilogram of animal body weight, and most preferably 0.12–0.17 grams of propionate per kilogram of animal body weight.

Preferably, the propionate is combined with a protein feed supplement to synergistically enhance the results. In that regard, the preferred protein supplements are cottonseed meal, feather meal, bone meal and combinations thereof. The preferred combination of propionate in such protein feeds is as follows: 3–22% by weight calcium propionate as a percentage of the daily feed, preferably 6–17% by weight calcium propionate as a percentage of the daily feed, and most preferably 9–13% by weight calcium propionate as a percentage of the daily feed. This works out to preferred ranges of 2–18% by weight propionate as a percentage of the daily feed, preferably 4–13% by weight propionate as a percentage of the daily feed, and most preferably 7–11% by weight propionate as a percentage of the daily feed.

It is a primary object of the present invention to provide an improved feed supplement to ruminants using propionate.

The primary advantages of the present invention are that the propionate is easy to administer to the ruminant, it reduces insulin insensitivity and increases body weight.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENT

In general, ruminants, after consuming a low energy diet (such as dormant range forage) for an extended time, show resistance to insulin as exhibited by prolonged glucose half-life (similar to a condition of type II diabetes in humans). The net effect is that nutrients are unable to pass from the serum into tissues. This condition then exacerbates low energy intake and stimulates metabolic inefficiencies. While feeding specific combinations of supplemental proteins to ruminants can increase the release of the hormone insulin, an increase in serum insulin will not improve energy metabolism unless the animal can respond to higher insulin concentrations. The methods and compositions of the present invention are useful for altering insulin sensitivity and thereby improving ruminant metabolism. The methods and compositions optionally comprise feeding combinations of supplemental proteins in combination with certain organic molecules.

In the preferred embodiment, the present invention is directed to reduction of blood glucose through use of organic acids, such as propionic acid (or salts thereof). In accordance with this embodiment, propionic acid stimulates tissue sensitivity to insulin, which results in enhanced glucose uptake by tissue. This effect is particularly suited to treatment of range cows that have been exposed to chronic periods of undernutrition or periods of nutritional stress (e.g., pregnancy and lactation). Such cows exhibit a diminished ability to respond to insulin, which in turn diminishes nutrient uptake. When glucose, or glucose precursors, are limiting nutrients, efficient energy metabolism is compromised.

In an alternative embodiment, a protein supplement is fed to ruminants in combination with an organic acid. For example, in the typical nutritional environment of a range cow grazing dormant vegetation, the stimuli to allow the animal to release insulin is lacking. If this ruminant is fed a bypass protein supplement (for example, but not limited to, feather/blood/cottonseed meal, or the feed formulations as set forth in U.S. Pat. Nos. 5,672,366 and 5,955,122), insulin release is stimulated. This is a very desirable effect if the animal has the capacity to respond to insulin. In instances where the animal has decreased insulin sensitivity (as a result of, for example, but not limited to, undernutrition) the addition of propionic acid (propionate) enhances the animal's response to insulin. The enhanced insulin sensitivity allows for greater nutrient flow to tissues. Moreover, glucose supply is increased, which has a dramatic effect if limiting. In accordance with this embodiment, propionate is added in combination with the protein supplement or added separately in addition to the protein supplement. Alternatively, the propionate is added to the diet without addition of a protein supplement. In general, the conditions of the animal/animals will dictate.

The preferred dosing for use as a ruminant supplement is in the range of 25 to 200 grams, preferably 50 to 150 grams, and most preferably 80 to 120 grams of calcium propionate for a typical cow weighing approximately 550 kilograms. Since there is approximately 80 percent propionate in calcium propionate, the preferred ranges are 20 to 160 grams of propionate, preferably 40 to 120 grams of propionate, and most preferably 64 to 96 grams of propionate per day for a typical cow weighing approximately 550 kilograms. This works out to preferred ranges of 0.04 to 0.29 grams of propionate per kilogram of animal body weight, preferably 0.07 to 0.22 grams of propionate per kilogram of animal body weight, and most preferably 0.12 to 0.17 grams of propionate per kilogram of animal body weight. For a feed supplement, the preferred ranges are 3 to 22% by weight calcium propionate as a percentage of the daily feed, preferably 6 to 17% by weight calcium propionate as a percentage of the daily feed, and most preferably 9 to 13% by weight calcium propionate as a percentage of the daily feed. This works out to preferred ranges of 2 to 18% by weight propionate as a percentage of the daily feed, preferably 4 to 13% by weight propionate as a percentage of the daily feed, and most preferably 7 to 11% by weight propionate as a percentage of the daily feed.

When both protein supplement and propionate are added to ruminant feed, a synergistic effect results. For example, range cows and sheep need higher insulin concentrations to direct nutrients to tissues (stimulated by the protein supplement) but the tissues also need to respond to insulin (stimulated by propionate). Thus, administration of protein supplement and propionate: (i) increases insulin via protein supplement; and (ii) increases insulin sensitivity. The combined effect often results in lower blood glucose levels due to increased tissue uptake of glucose.

EXAMPLE

A study was conducted with 50 postpartum two-year old cows. Cows were individually fed one of three supplements. They were fed at a rate of 908 g/day (3.5 times the daily rate twice per week) a feed that contained 36% crude protein as follows in Table 1. The control supplement comprised mostly cottonseed meal.

TABLE 1

Feed Formulation

| Ingredient | As Fed % |
|---|---|
| cottonseed meal | 33.0 |
| wheat middlings | 22.7 |
| hydrolyzed poultry feather meal | 15.0 |
| blood meal | 5.0 |
| calcium propionate | 11.0 |
| molasses | 9.0 |
| potassium chloride | 1.8 |
| dicalcium phosphate | 1.4 |
| urea | 0.7 |
| Vitamin A premix | 0.15 |
| trace minerals | 0.1 |

This supplement has a nutrient analysis as shown in Table 2.

TABLE 2

Supplement Nutrient Analysis Fed Twice Per Week to Two-Year Old Cows Grazing Winter Range

| Nutrient | As Fed % |
|---|---|
| crude protein | 39.6 |
| crude protein undergradable intake (UIP) | 18.0 |
| TDN | 57.6 |
| crude fat | 2.7 |
| crude fiber | 6.6 |

TABLE 2-continued

Supplement Nutrient Analysis Fed Twice Per Week to Two-Year Old Cows Grazing Winter Range

| Nutrient | As Fed % |
|---|---|
| calcium | 2.9 |
| phosphorus | 1.0 |
| potassium | 2.0 |
| Vitamin A, IU | 30000 |
| dry matter | 91.0 |

A second supplement was formulated with cottonseed meal, blood meal and feather meal. The third supplement was identical to the second except it contained approximately 100 g of a calcium propionate salt (approximately 80 g as propionic acid).

The results are shown in Table 3.

TABLE 3

Influence Of Propionate Salt Added To A Protein Supplement On 2-Year Old Post Partum Cow Serum Glucose Half-Life (Minutes), Insulin And Glucose Area Under The Curve (AUC) In Response To A Glucose Challenge

| | Supplement | | | |
|---|---|---|---|---|
| Measurement | Cottonseed Meal | Cottonseed, Blood & Feather Meal | Plus Propionate | P |
| Glucose half-life, min. | 62 ± 5 | 54 ± 5 | 44 ± 5 | <.03 |
| Glucose AUC | 15289 ± 543 | 14604 ± 543 | 13057 ± 543 | <.01 |
| Insulin, AUC | 291 ± 49 | 273 ± 49 | 288 ± 49 | >.79 |
| Initial calving weight[1] lb | 753 | 761 | 772 | >.83 |
| End breeding season weight[2], lbs. | 813 | 818 | 864 | <.05 |
| Elevated serum progesterone[3], % | 71 | 80 | 85 | <.05 |

[1]Body weight recorded March 9, 2000.
[2]Body weight recorded July 7, 2000.
[3]Cows with elevated serum progesterone concentrations are predicted to be pregnant.

The results demonstrate that the consumption of propionate salts added to the protein supplements decrease serum glucose half-life (by approximately 10 to approximately 18 minutes depending on the feed composition as shown in Table 3) while secreting the same quantity of insulin; thus demonstrating enhanced insulin sensitivity due to the consumption of propionate salts. Feeding propionate serves as a method of increasing insulin sensitivity. This effect improves body weight change, body condition score and reproduction measures in young ruminants.

A more detailed presentation of the results appears below in Table 4.

TABLE 4

Influence of Propionate Salt Added to a Protein Supplement on Two-Year-Old Post-Partum Cow Body Weight Change from Calving to the Termination of Breeding.

| | SUPPLEMENT | | | |
|---|---|---|---|---|
| Date | Weight Using Cotton-seed Meal (lbs) | Weight Using Cotton-seed, Blood & Feather Meal (lbs) | Weight Using CSM, BM, FM[1] Plus Propionate (lbs) | P |
| Calving (supplementation started) | | | | |
| 3/03 | 753 | 761 | 772 | 0.83 |
| 3/06 | 757 | 754 | 794 | 0.29 |
| 3/20 | 738 | 750 | 781 | 0.19 |
| 4/03 | 712 | 712 | 741 | 0.34 |
| 4/17 | 719 | 728 | 756 | 0.32 |
| Begin breeding | | | | |
| 5/01 | 726 | 736 | 749 | 0.56 |
| 5/16 | 766 | 773 | 796 | 0.35 |
| Supplementation ended | | | | |
| 5/29 | 784 | 799 | 817 | 0.35 |
| 6/09 | 784 | 797 | 806 | 0.55 |
| 6/26 | 788 | 800 | 824 | 0.39 |
| Terminate breeding | | | | |
| 7/7 | 813 | 818 | 864 | 0.05 |
| Difference from CSM, BM & FM fed cows | | | | |
| 3/03 to 7/07 | −36 | −32 | 0 | |

[1]CSM = cottonseed meal
BM = blood meal
FM = feather meal
Propionate = calcium propionate This invention is not limited to the specific meal compositions disclosed above. Other preferred feed compositions to which propionate is added, in accordance with the present invention, are disclosed in U.S. Pat. Nos. 5,672,366 and 5,955,122, incorporated herein by reference. Other meal compositions may be utilized in accordance with the present invention. Nor is the present invention limited to oral administration with meal. Thus, traditional administration of substances to ruminants known in the art are within the scope of the present invention, including, but not limited to, liquid administrations, implantable delivery systems and/or injections. Likewise, other salts, and other propionate salts (e.g. besides calcium) may also be utilized in accordance with the present invention. Further, the number of doses may be varied, depending upon the ruminant and the form of administration and propionate.

While the results presented were for formulations using calcium propionate, other forms of propionate and/or propionic acid are suitable. Such other forms include, but are not limited to, dry, aqueous and/or other solvent diluted forms. Therefore, sodium propionate ($NaC_3H_5O_2$) is within the scope of the present invention. Sodium propionate has also been demonstrated to have effective use in ketoses of ruminants (glucose precursor). It has also been effective for use in treating dermatoses, go wound infections, and conjunctivitis. A traditional use of propionic acid salts has been as an antifungal, for example, to control molds and mycoitoxins.

Calcium propionate in mono- and/or trihydrate forms are also within the scope of the present invention. While soluble in water, this salt is also soluble in methanol, ethanol, and other solvents. Propionic acid is soluble in water, alcohol, ether, and chloroform, among other solvents. Propionic acid is also useful as an esterifying agent for cellulose.

The present invention, as disclosed, shows that propionate treatment does indeed have benefits for ruminants.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method to reduce insulin insensitivity and increase body weight in ruminants who are insulin insensitive comprising the following steps of:

providing propionate in an amount of at least 5 grams per day as a supplement to the insulin insensitive ruminant.

2. The method of claim 1 wherein the step of providing propionate comprises providing calcium propionate.

3. The method of claim 1 wherein the step of providing propionate comprises providing propionic acid.

4. The method of claim 1 wherein the step of providing propionate comprises providing sodium propionate.

5. The method of claim 1 wherein the step of providing propionate comprises feeding the propionate to the ruminant as a feed supplement.

6. The method of claim 1 wherein the step of providing propionate comprises using at least one method selected from the group consisting of liquid administration, implantable delivery system and injection.

7. The method of claim 1 further comprising the step of providing protein as a supplement to the ruminant.

8. The method of claim 7 wherein the step of providing protein comprises providing cottonseed meal.

9. The method of claim 7 wherein the step of providing protein comprises providing blood meal.

10. The method of claim 7 wherein the step of providing protein comprises providing feather meal.

11. The method of claim 10 wherein the step of providing protein further comprises providing blood meal.

12. The method of claim 9 wherein the step of providing protein further comprising providing feather meal.

13. The method of claim 9 wherein the step of providing protein further comprises providing cottonseed meal.

14. The method of claim 1 wherein the step of providing propionate comprises providing propionate in an amount of between approximately 0.04 grams and 0.29 grams of propionate per kilogram of ruminant body weight.

15. The method of claim 14 wherein the step of providing propionate comprises providing propionate in an amount of between approximately 0.07 grams and 0.22 grams of propionate per kilogram of ruminant body weight.

16. The method of claim 15 wherein the step of providing propionate comprises providing propionate in an amount of between approximately 0.12 grams and 0.17 grams of propionate per kilogram of ruminant body weight.

17. The method of claim 5 wherein the step of providing propionate comprises providing between approximately 2 percent by weight and 18 percent by weight propionate as a percentage of said feed.

18. The method of claim 17 wherein the step of providing propionate comprises providing between approximately 4 percent by weight and 13 percent by weight propionate as a percentage of said feed.

19. The method of claim 18 wherein the step of providing propionate comprises providing between approximately 4 percent by weight and 13 percent by weight propionate as a percentage of said feed.

* * * * *